(12) United States Patent
Mazuyer et al.

(10) Patent No.: US 7,752,883 B2
(45) Date of Patent: Jul. 13, 2010

(54) TRIBOMETER

(75) Inventors: Denis Mazuyer, Ecully (FR); Andre Large, Lyons (FR)

(73) Assignees: Centre National de la Recherche Scientifique, Paris (FR); Ecole Centrale de Lyon, Ecully (FR)

( * ) Notice: Subject to any disclaimer, the term of this patent is extended or adjusted under 35 U.S.C. 154(b) by 729 days.

(21) Appl. No.: 10/587,610

(22) PCT Filed: Feb. 2, 2005

(86) PCT No.: PCT/FR2005/050063

§ 371 (c)(1),
(2), (4) Date: May 14, 2007

(87) PCT Pub. No.: WO2005/075956

PCT Pub. Date: Aug. 18, 2005

(65) Prior Publication Data

US 2008/0034837 A1 Feb. 14, 2008

(30) Foreign Application Priority Data

Feb. 3, 2004 (FR) .................................. 04 01017

(51) Int. Cl.
*G01N 3/56* (2006.01)

(52) U.S. Cl. ............................................................ 73/9

(58) Field of Classification Search ...................... 73/9, 73/10, 819, 788
See application file for complete search history.

(56) References Cited

U.S. PATENT DOCUMENTS

| 2,106,170 | A |   | 1/1938  | Faville ............................. 73/10 |
| 5,319,257 | A | * | 6/1994  | McIntyre ....................... 310/328 |
| 5,795,990 | A | * | 8/1998  | Gitis et al. ........................ 73/9 |
| 5,955,655 | A |   | 9/1999  | Evans ................................ 73/7 |
| 6,145,370 | A |   | 11/2000 | Evans ................................ 73/7 |
| 6,776,048 | B2 | * | 8/2004 | Corrias et al. .................. 73/819 |

FOREIGN PATENT DOCUMENTS

| FR | 1 500 941   | 11/1967 |
| FR | 2 036 123   | 12/1970 |
| JP | A 61-102539 | 5/1986  |

* cited by examiner

*Primary Examiner*—Hezron Williams
*Assistant Examiner*—Tamiko D Bellamy
(74) *Attorney, Agent, or Firm*—Oliff & Berridge, PLC

(57) ABSTRACT

The present invention relates to a tribometer (1) comprising: a first support assembly (2) configured to receive a central test piece (3), which test piece is circularly cylindrical, and to drive it in rotation about its axis (X); and a second support assembly (4) configured to receive a plurality of peripheral test pieces, preferably three of them, and to enable said central test piece (3) to make contact simultaneously with said three peripheral test pieces (9) in an isostatic configuration in such a manner that the central test piece, while being driven in rotation, can rub against the peripheral test pieces.

16 Claims, 8 Drawing Sheets

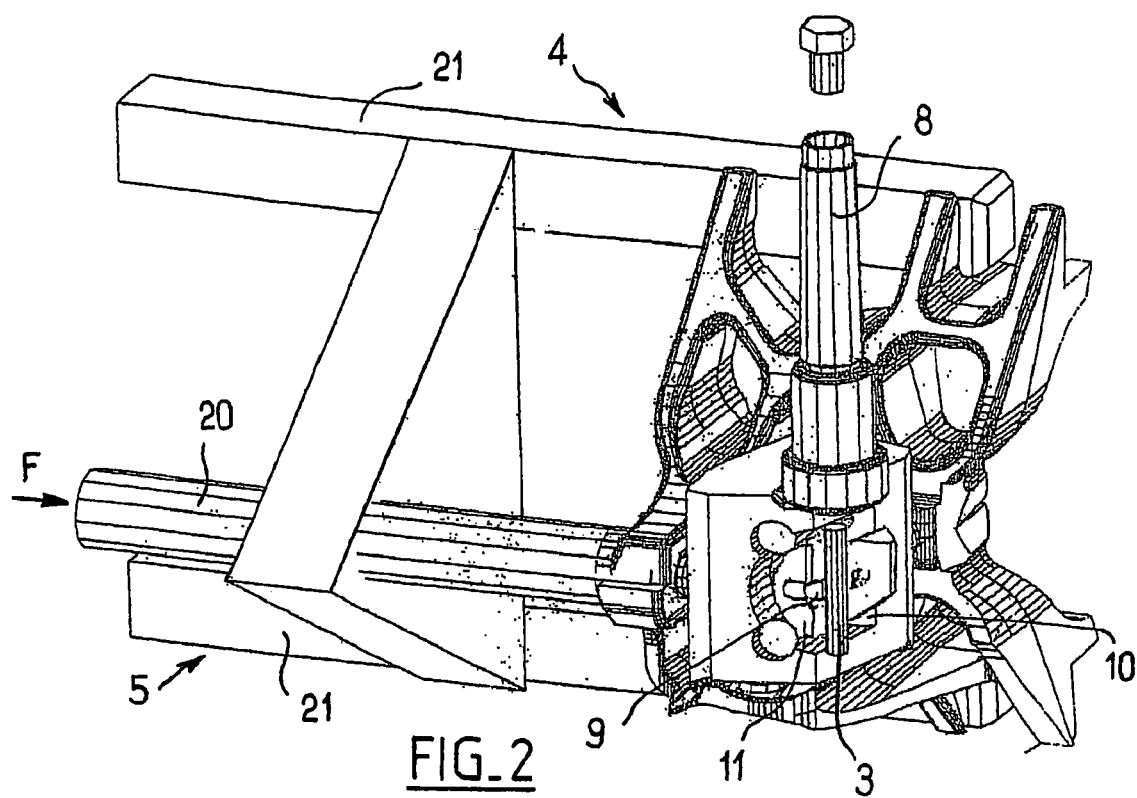
FIG_2
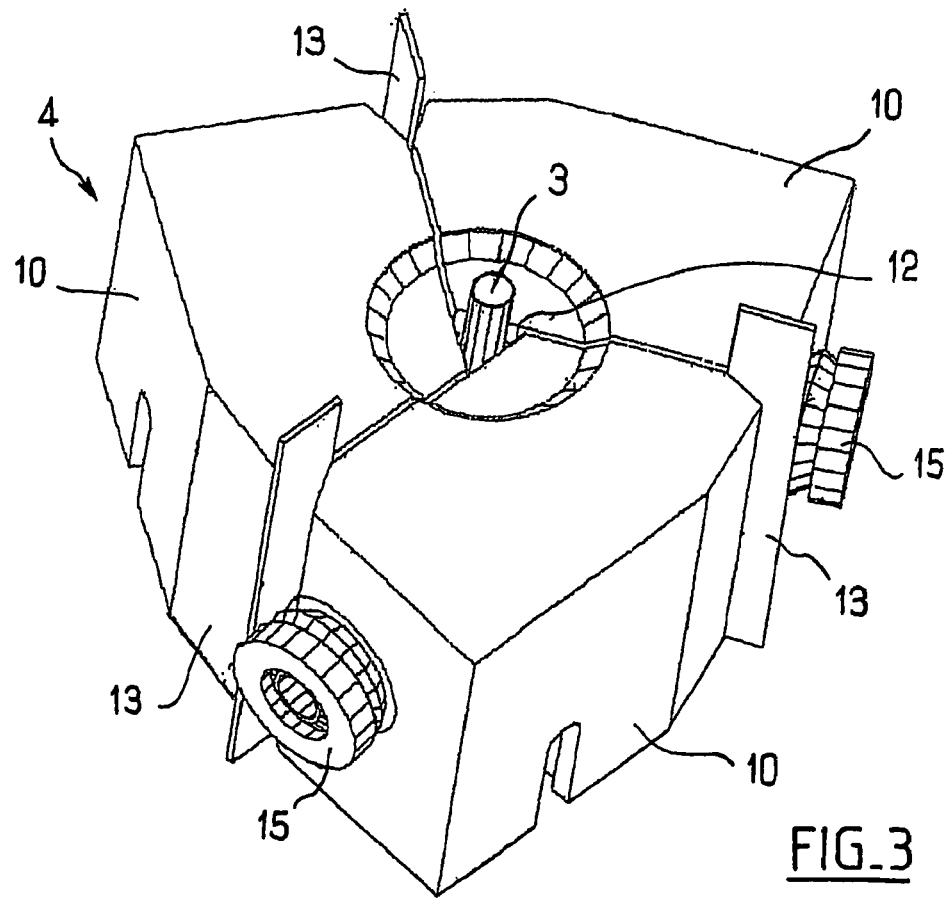
FIG_3

FIG_6

FIG_7

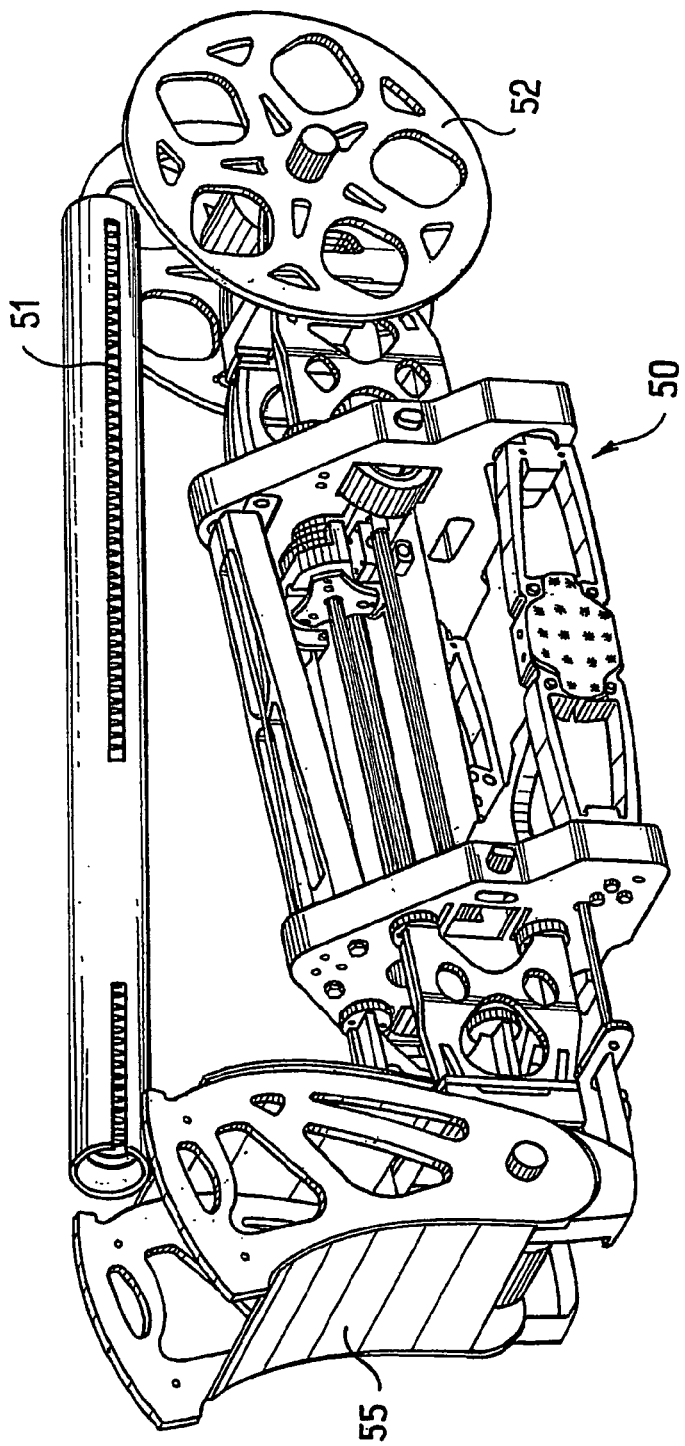
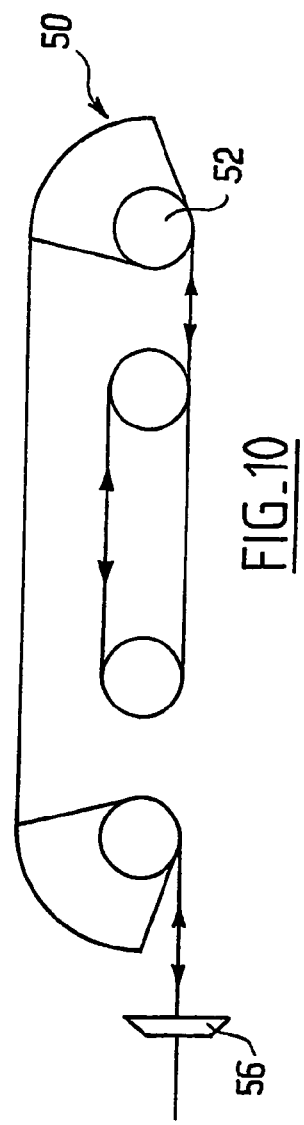
FIG_9
FIG_10

TRIBOMETER

The invention relates to a tribometer serving in particular to generate contact pressures and/or sliding friction velocities that are very high.

In certain fields of production, such as forming metals, improving productivity and reducing maintenance costs require the contacts between optionally lubricated friction surfaces to be subjected to operating conditions that are becoming more and more severe. By way of example, mention can be made of the process for drawing brass-plated steel wires in the manufacture of radial tire carcasses, which process remains one of the most complex in terms of lubrication. Steels of ever-increasing elastic limit are transformed at ever-faster velocities. New higher-performance formulations of lubricant need to be devised in order to be able to draw hard steel wires well at extremely high velocities, and also to work other metals.

Furthermore, in order to predict the lifetime of a mechanical system (motor, transmission, bearings), it is necessary to accelerate the aging process of the friction surfaces by increasing the severity of the tribological conditions to which the surfaces are subjected, and in particular by increasing the wear rate of the surfaces. This can make it possible to reduce heavy and expensive testing on industrial test benches.

Three parameters are particularly crucial for understanding wear phenomena and lubrication mechanisms at high pressures and high speeds:
- contact temperature, which can be greater than 500° C., and which can limit the real performance of lubricants;
- contact time which can be very short (of the order of a few microseconds (μs)) if sliding velocities are very high (greater than 1 meter per second (m/s)); and
- the pressure gradient to which the lubricant is subjected as it passes into contact between the friction surfaces.

In conventional manner, the tribological behavior of surfaces and lubricants is initially evaluated at relatively low pressures and velocities, that are accessible to conventional tribometers such as those sold by the suppliers Falex and Plint & Partners, and then the results obtained are extrapolated for velocities and pressures that are significantly higher, by using correlations that are based on a large number of validation tests on industrial test benches.

Those conventional tribometers present certain drawbacks:
- the test pieces used can be expensive due to being complex in shape, some being cylindrical in shape with a wedge;
- running the tests can be expensive;
- operating conditions can be insufficient for testing materials possessing high resistance to wear such as ceramics or certain steels;
- it is difficult or even impossible to apply high velocities and high pressures simultaneously, with velocities generally being limited to about 0.1 m/s and maximum contact pressures being of gigapascal (GPa) order; and
- it is difficult or even impossible simultaneously to control contact dynamics and loading rates on the contacts.

The invention seeks to remedy the above drawbacks in full or in part.

The invention provides a tribometer comprising:
- a first support assembly configured to receive a central test piece, which test piece is circularly cylindrical, and to drive it in rotation about its axis; and
- a second support assembly configured to receive a plurality of peripheral test pieces, preferably three of them, and to enable said central test piece to make contact simultaneously with said three peripheral test pieces in an isostatic configuration in such a manner that the central test piece, while being driven in rotation, can rub against the peripheral test pieces.

By means of the invention, it is possible to carry out tests with test pieces that are simple in shape and thus inexpensive to fabricate.

Preferably, at least one of the three peripheral test pieces, and in particular all three of them, presents a shape selected in such a manner as to enable contact with the central test piece to be linear, in particular along a straight line segment. This makes it possible in particular to generate increased losses of material and to have wear surfaces of relatively large area that can be used for characterizing the chemical transformations of these surfaces as a result of tribological stressing.

At least one of the three peripheral test pieces, and in particular all three of them, may comprise a plane face whereby it rubs against the central test piece, and each may for example be in the form of a plate.

The test pieces can thus be particularly simple in shape, thereby enabling the cost of fabricating them to be reduced significantly. This is particularly advantageous for ceramic materials such as tungsten carbide or alumina.

Preferably, the second support assembly is configured in such a manner that the contacts between the peripheral test pieces and the central test piece are distributed at equal angles around said central test piece, being substantially at 120° intervals from one another, with contact between the central test piece and the group of three peripheral test pieces being isostatic.

By driving the central test piece at a high rotary velocity and/or by increasing the diameter of the central test piece, the invention makes it possible to reach very high sliding friction velocities, in particular greater than 1 m/s, and possibly as fast as 15 m/s. The above-mentioned isostatic contact can also make it possible to reach very high contact pressures, in particular pressures greater than 1 GPa, e.g. up to 3 GPa.

Since the contacts are subjected to very severe tribological stresses, similar to those of real operating conditions, tests on test benches can be reduced, thus making it possible to limit development costs.

The invention also makes it possible to facilitate formulating lubricant fluids (liquid, solid, multiphase, emulsion, dispersion, aqueous lubricant, solid lubricant, oil, grease) and to prepare materials for mechanical systems that are stressed under very severe conditions of pressure, sliding velocity, and contact temperature.

The invention is particularly well adapted to testing metals and ceramics having very high resistance to wear, such as tungsten carbide, in which wear occurs only above energy thresholds that are high, of the order of 1 kilojoule per cubic micrometer ($kJ/\mu m^3$).

The invention also makes it possible:
- to establish maps for friction, pressure, and velocity coefficients for a given material-and-lubricant pair, thus making it possible to refine optimum lubrication conditions;
- to study thermal effects on lubrication under very high velocity and pressure conditions by using high velocities associated with continuous measurement of the average contact temperature; and
- to carry out fundamental investigations on wear processes and lubrication mechanisms, under extreme velocity and pressure conditions. In these velocity and pressure ranges, the tribological behavior of lubricants and of the surfaces they protect is poorly known because it is difficult at present to simulate such conditions away from industrial test benches.

The second support assembly may comprise three support parts, each carrying a respective test piece, at least one of these three support parts possibly being movable relative to the other two.

The three support parts may be configured to form a cavity suitable for containing a fluid, in particular a lubricant, the central and peripheral test pieces possibly extending at least in part in said cavity so that the contacts between the central test piece and the peripheral test pieces can be immersed at least in part in the fluid, where appropriate.

The tribometer of the invention thus makes it possible to test contacts that are dry or lubricated.

The tribometer may comprise a circuit configured to establish circulation of the fluid, in particular lubricant, within the cavity.

Such circulation can make it possible to control temperature within the cavity.

The tribometer may comprise a load-application device configured to apply a force on at least one of the support parts, and in particular on all three of them.

The load-application device may comprise three pushers each configured to exert on a respective one of the support parts a force that is substantially normal to the axis of rotation of the central test piece.

Each pusher may be driven by an actuator comprising a hinged arm secured at one end to a stationary portion of the tribometer, and at its other end to an axially movable drive member.

Advantageously, the tribometer comprises a load-sharing device configured to control the load-application device, in particular by controlling the displacement of the drive members of the load-application device.

Each drive member is advantageously secured to a drive pulley, and the load-sharing device may comprise a belt configured on the pulleys of the drive members, with the load-sharing device also being configured to exert variable tension on the belt.

The tribometer of the invention can act in real time to regulate the load applied on the test pieces.

The load-sharing device may comprise two pulleys for guiding the belt, each disposed between two drive pulleys.

The load-sharing device may also comprise two load pulleys having the two ends of the belt secured respectively thereto.

At least one of the load pulleys may be driven in rotation by means of a strip fixed at one end to the load pulley and at its other end to a moving carriage.

The load-sharing device may comprise a first flexible membrane configured to drive displacement of the moving carriage as a function of the pressure within the first membrane.

In an embodiment of the invention, the tribometer comprises a pressure-regulation system configured to control the pressure of the first membrane, said system comprising, for example, a spring having a first end suitable for being moved by a motor and a second end secured to an arm that is configured to act on a second flexible membrane in communication with the first flexible membrane.

The tribometer of the invention can thus serve to control simultaneously the loading rate and the contact dynamics.

The tribometer may be configured to make it possible to reach a maximum load of $2 \times 10^4$ newtons (N) per pusher in 4 s, giving a maximum pressure gradient of about 7000 bars per second.

The load-application and load-sharing devices and the pressure-regulation system are external to the above-mentioned cavity and need never come directly into contact with the lubricant.

The tribometer may be configured to act on the position of at least one of the support parts in the event of displacement of a contact between the central test piece and one of the peripheral test pieces.

The load device may be associated with a tangential force sensor suitable for measuring tangential force at one of the contacts between the central test piece and one of the peripheral test pieces.

Continuous measurement of the drive torque driving the central test piece in rotation makes it possible to evaluate precisely the friction forces on the other two contacts that are not associated with a tangential force sensor.

The tribometer may have three normal force sensors configured to measure the normal force acting on each contact between the central test piece and the peripheral test pieces.

The invention can be better understood on reading the following detailed description of a non-limiting embodiment of the invention, and on examining the accompanying drawings, in which:

FIG. 2 is a diagrammatic and fragmentary view of the contacts between the test pieces;

FIG. 3 is a diagrammatic and fragmentary view of the second support assembly of the FIG. 1 tribometer;

FIG. 9 is a diagrammatic and fragmentary view of a pressure-regulation system of the tribometer; and FIG. 10 is a diagrammatic view of the pressure-regulation system of the tribometer.

FIG. 1 shows the various elements constituting a tribometer 1 in accordance with the invention.

Figure 1:
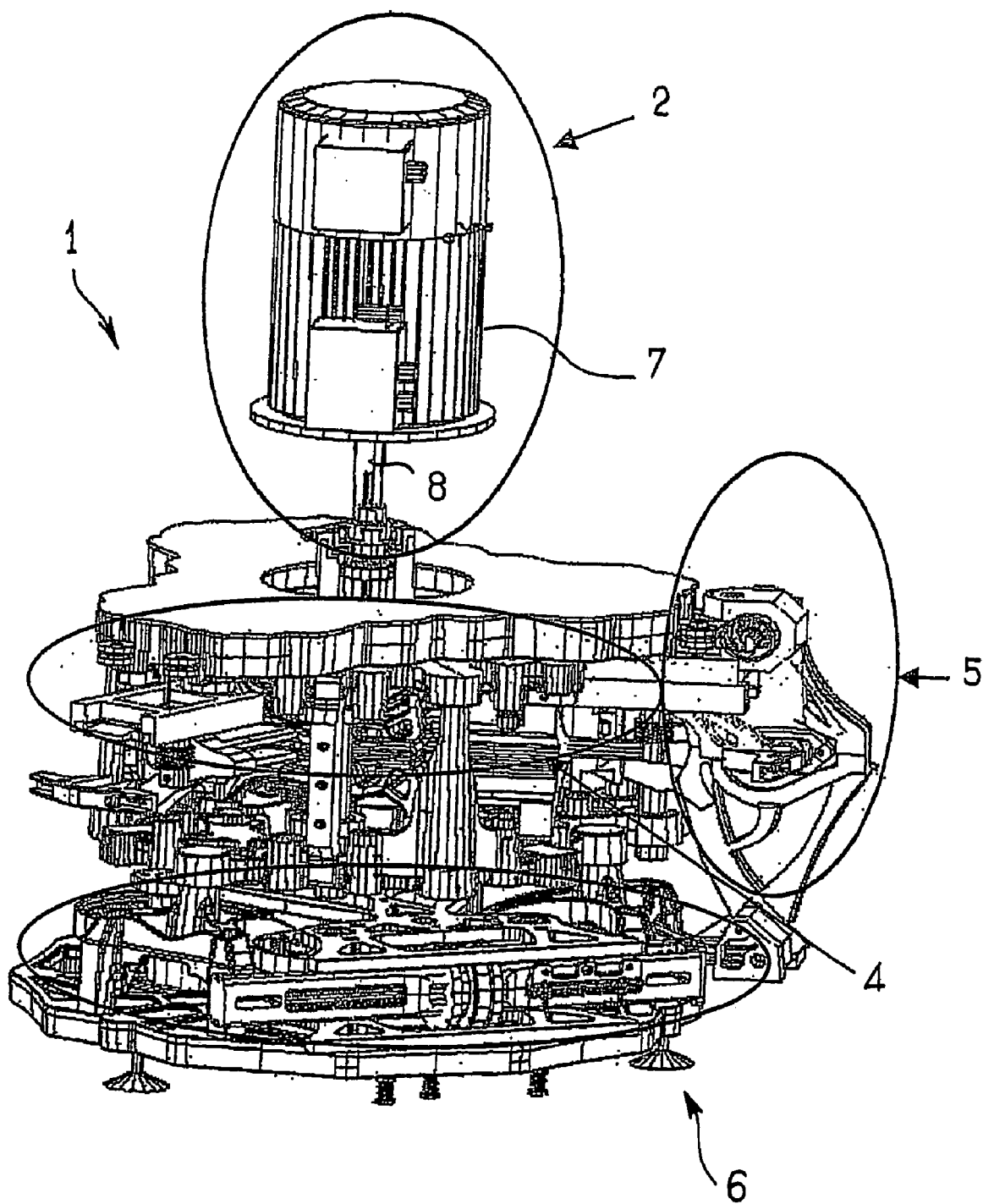
FIG. 1 is a diagrammatic and fragmentary perspective view of a tribometer in accordance with the invention.

The tribometer 1 comprises a first support assembly 2, a second support assembly 4, a load-application device 5, and a load-sharing device 6.

The first support assembly 2 carries a central test piece 3 that is circularly cylindrical.

The central test piece 3 is secured to a shaft of axis X of a drive motor 7 by means of a spindle 8 configured to enable test pieces to be installed of diameter lying in the range 8 mm to 32 mm in the example described.

The motor 7 is configured to drive the test piece 3 in rotation at a speed that may be as high as 9000 revolutions per minute (rpm), thus enabling linear speeds to be reached lying in the range about 3.8 m/s to 15 m/s.

The second support assembly 4 has three support parts 10, as can be seen in FIGS. 2 and 3.

Each support part 10 carries a peripheral test piece 9 that is in the form of a plate, e.g. made of stainless steel, the plate being inserted in a setback in the support part 10 and being held therein by snap-fastening, in the example described.

Each support part 10 presents a recess 11 suitable for co-operating with the two recesses 11 of the other two support parts 10 when all three parts 10 are united as shown in FIG. 3, to define a cavity 12 in which the three peripheral test pieces 9 are received and in which it is possible to engage the central test piece 3 while the tribometer is in operation.

Sealing gaskets 13 may be interposed between each pair of support parts 10, as can be seen in FIG. 3, so as to seal the cavity 12.

The cavity 12 can be used as a container for a lubricant, in particular a liquid lubricant, with the contacts between the central test piece 3 and the peripheral test pieces 9 being immersed therein.

The cavity 12 can be put into communication with a circuit configured to cause a fluid, in particular a lubricant, to circulate in the cavity 12 via two orifices 15, respectively an inlet and an outlet, configured in two of the support parts 10.

The load-application device 5 comprises three pushers 20 each suitable for exerting a normal force F on a respective one of the support parts 10, as shown in FIG. 2.

By applying a very high force F (up to about $2 \times 10^4$ N), it is possible to reach very high contact pressures (up to about 3 GPa).

Figure 6:
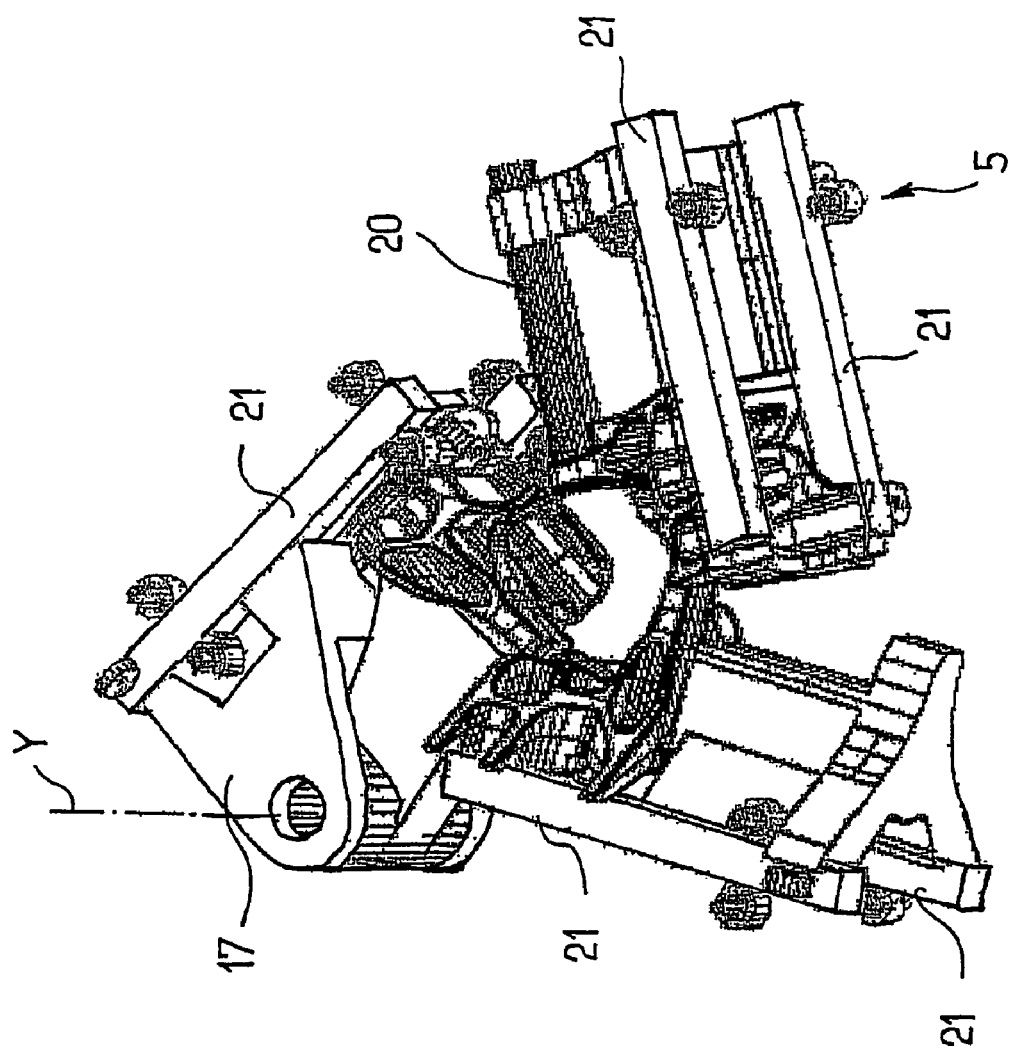
FIG. 6 is a diagrammatic and fragmentary perspective view of the load-application device of the tribometer.

Each pusher 20 is slidably mounted on rails 21, as can be seen in FIGS. 2 and 6.

For reasons of clarity, only one of the three pushers 20 is shown in FIG. 6.

Figure 4:
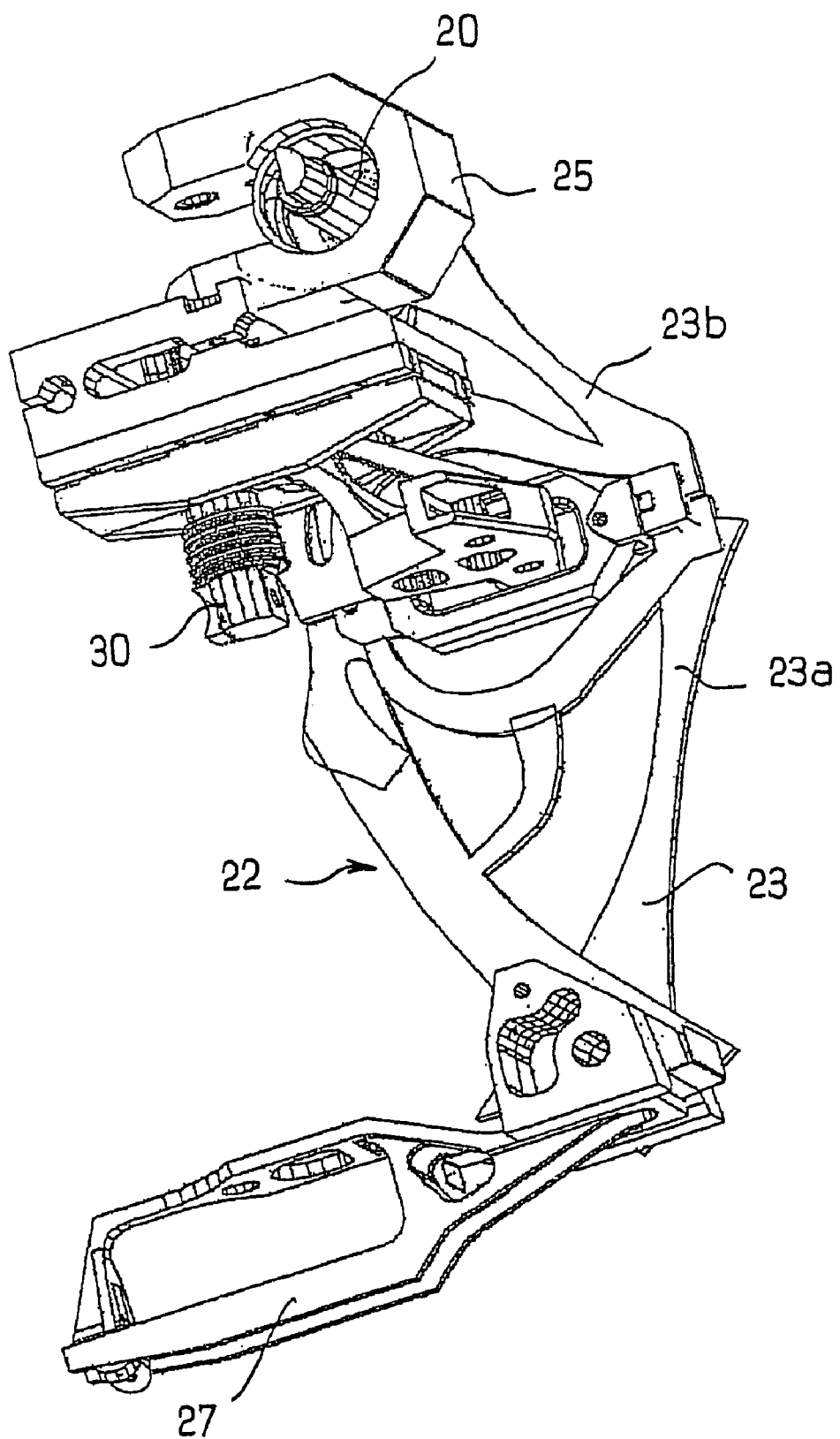
FIG. 4 is a diagrammatic and fragmentary view of the load-application device of the tribometer.

Each pusher 20 is controlled in displacement by a respective actuator 22, shown in FIG. 4.

The actuator 22 comprises a pivot arm 23 presenting a bottom portion 23a and a top portion 23b that are hinged together.

Figure 5:
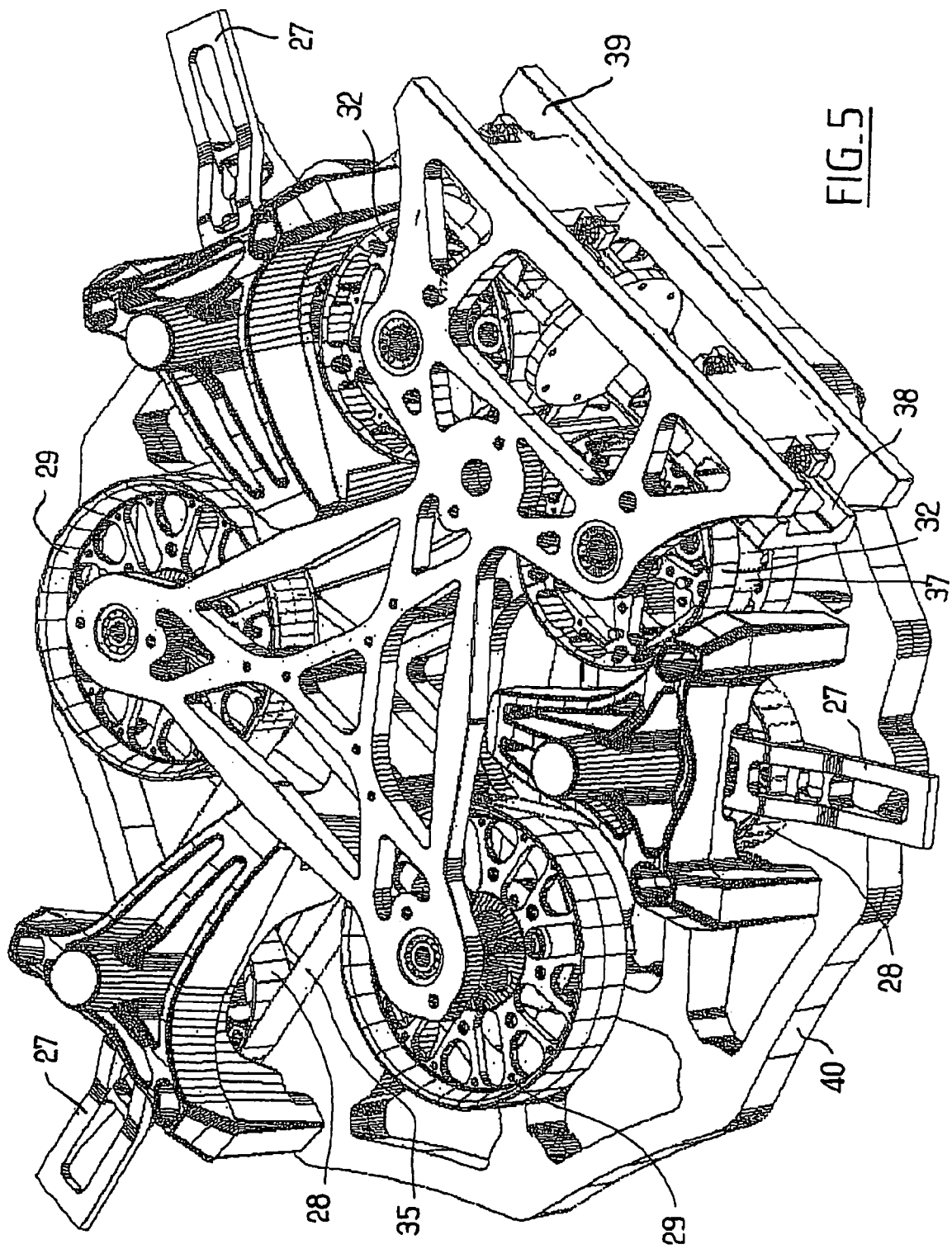
FIG. 5 is a diagrammatic and fragmentary perspective view of the load-sharing device of the tribometer.

The bottom portion 23a of the arm 23 is hinged on a drive member 27 slidably mounted on a frame 40 of the tribometer 1, as can be seen in particular in FIG. 5.

The top portion 23b of the arm 23 is hinged on a stationary portion 25 of the tribometer.

The actuator 22 comprises a resilient return element, in particular a spring (not shown), serving to return the pivot arm 23 towards a rest position. The spring also serves to filter parasitic variations in load.

The load device 5 comprises three normal force sensors 30 disposed close to the pusher 20 and serving to measure the normal force applied thereto, together with an additional sensor (not shown) serving to measure a tangential force on one of the friction contacts.

The normal force sensor 30 is advantageously placed after the above-mentioned resilient return element.

As can be seen in FIG. 6, the load device 5 comprises an assembly 17 mounted to pivot about an axis Y and carrying a pusher 20 (not shown) for applying a normal force on a support part 10.

The assembly 17 is associated with the above-mentioned additional sensor, which can be constituted by a normal force sensor, so that when the assembly 17 pivots about the axis Y, it comes to press against the additional sensor.

By measuring a normal force, this sensor thus serves to determine the tangential force on one of the friction contacts.

In addition, pivoting the assembly 17 about the axis Y makes it possible, in operation, to compensate for any offset between the friction contacts.

Each drive member 27 carries a drive pulley 28, as can be seen in FIG. 5.

The frame 40 carries firstly two guide pulleys 29 each configured between two drive pulleys 28, and secondly to load pulleys 32.

In the example described, the drive pulleys 28 have a diameter of 150 mm while the guide pulleys 29 have a diameter of 250 mm.

The load pulleys 32 comprise respective top portions with a diameter of 175 mm and bottom portions with a diameter of 200 mm.

A belt 35, made of Kelvar® in the example described, is engaged against the drive pulleys 28 from the outside and against the guide pulleys 29 from the inside, and it is secured at its ends to the load pulleys 32.

Each load pulley 32 is rotated by a strip 37, in particular a metal strip, having one end connected to the bottom portion of the load pulley 32 and the other end connected to a carriage 38 mounted to slide on a support 39.

Figure 7:
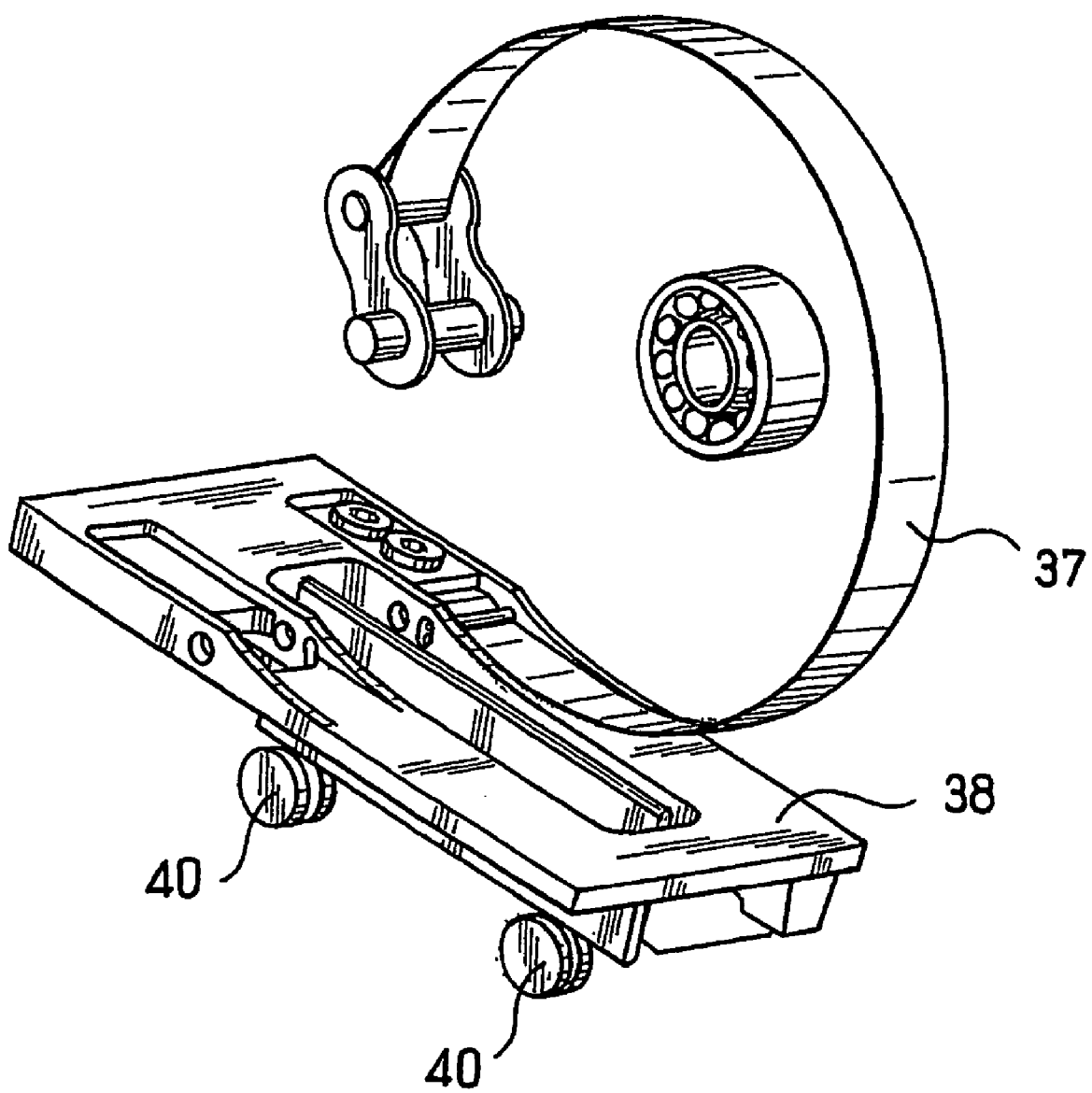
FIG. 7 is a diagrammatic and fragmentary view showing the moving carriage of the load device in isolation.

Each carriage 38, as shown in FIG. 7, has wheels 40 suitable for sliding on the support 39.

Figure 8:
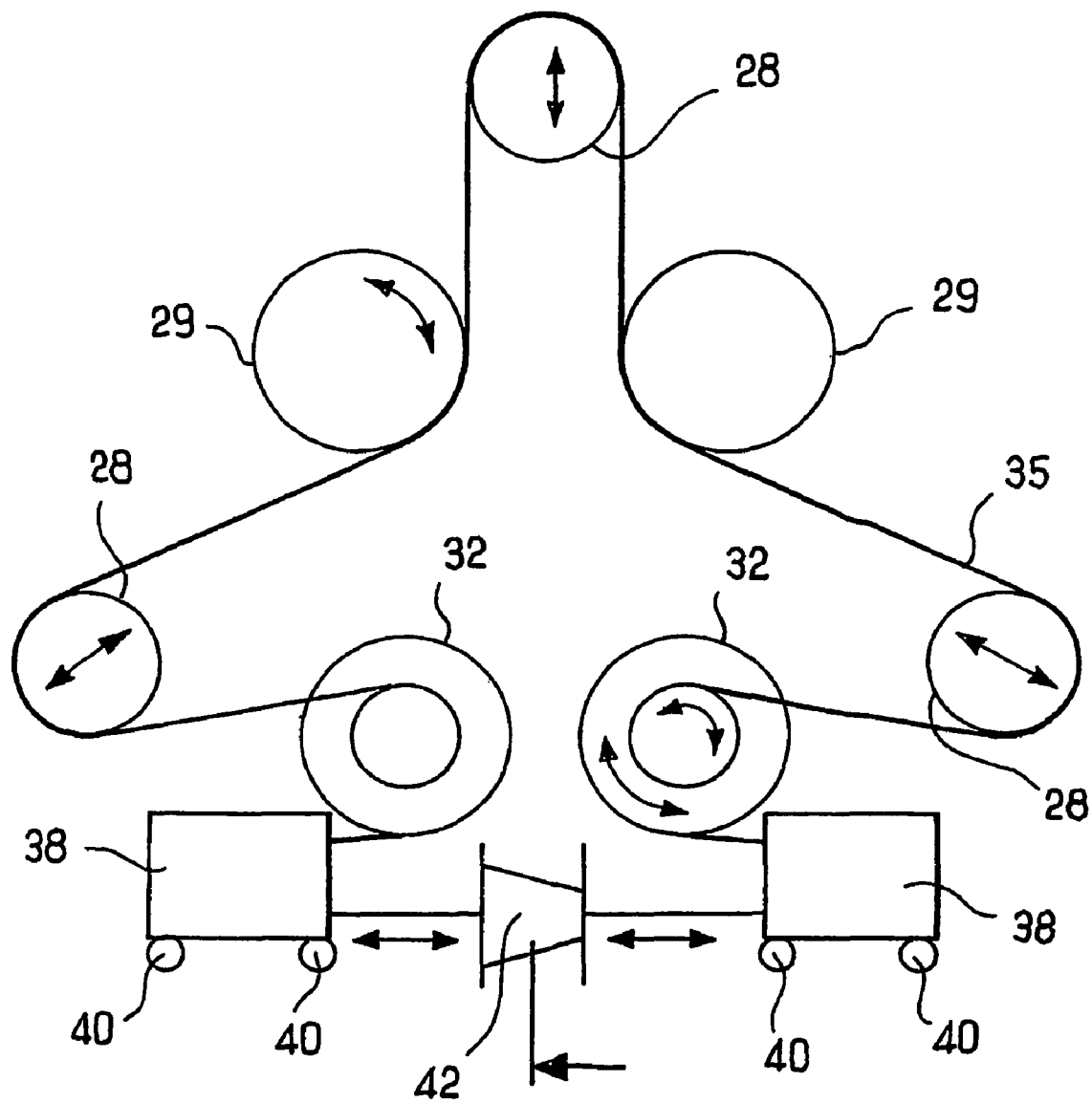
FIG. 8 is a diagrammatic view of the elements of the load-sharing device of the tribometer.

As can be seen in the diagram of FIG. 8, when the belt 35 is tensioned by displacement of the carriages 38, the belt drives the drive pulleys 28 inwards so that the actuators 22 drive the corresponding pushers 20 so as to exert a predetermined force on the support part 10.

Displacement of the carriages 38 is driven by deforming a first flexible membrane 42 disposed on the support 39 between the two carriages 38.

The first membrane 42 is associated with a pressure-regulator system 50 for controlling the pressure in the first membrane 42.

As can be seen in FIG. 9, the system 50 comprises a spring 51 connected at one end to a pulley 52 which pulley is turned by a motor (not shown).

The spring 51 is secured at its other end to an arm 55 serving to vary the pressure in a second flexible membrane 56 (shown in FIG. 10), said membrane being in communication via a tube with the first flexible membrane 42.

The following measurements have been taken during operation of the tribometer:

tangential force measurements in a range 0 to 5000 N, measured to within 0.08 N and regulated on 0.5 N on one contact;

measurements of the normal force on each contact over a range 0 to 20,000 N, measured to within 2 N and regulated on 1 N;

measurement of driving torque;

measurement of contact temperature to within 0.1° C.; and regulation and measurement of lubricant temperature when contact is lubricated to within 0.1° C.

The tribometer 1 enables the load to be applied and regulated with it being possible to subject the contact to controlled dynamic loading up to $2 \times 10^4$ N while mastering the contact dynamics at high speed.

The invention claimed is:

1. A tribometer comprising:

a first support assembly configured to receive a central test piece, which test piece is circularly cylindrical, and to drive it in rotation about its axis;

a second support assembly configured to receive three peripheral test pieces and to enable said central test piece to come simultaneously into contact with said three peripheral test pieces in an isostatic configuration, such that while being driven in rotation the central test piece can rub against the peripheral test pieces, the second support assembly comprising three support parts each carrying a respective peripheral test piece, each of these three support parts being movable relative to the other two, wherein the load-application device comprises three pushers configured to exert on each of the respective support parts a force that is substantially normal to the axis of rotation of the central test piece, each pusher being driven by an actuator comprising a hinged arm secured at one end to a stationary portion of the tribometer, and at its other end to a moving drive member; and a load-sharing device for controlling the displacement of the drive members, wherein each drive member is secured to a drive pulley, and by the fact that the load-sharing device comprises a belt engaged on the three drive pulleys, the load-sharing device being configured to exert variable tension on the belt.

2. A tribometer according to claim 1, wherein at least one of the three peripheral test pieces, presents a shape selected in such a manner as to enable contact with the central test piece to be linear.

3. A device according to claim 1, wherein at least one of the three peripheral test pieces and in particular all three of them, comprises a plane face whereby it rubs against the central test piece.

4. A tribometer according to claim 3, wherein at least one of the three peripheral test pieces, and in particular all three of them, presents the form of a plate.

5. A tribometer according to claim 1, wherein the second support assembly is configured in such a manner that the contacts between the peripheral test pieces and the central test piece are distributed at equal angles around said central test piece.

6. A tribometer according to claim 1, wherein the three support parts are configured to form a cavity suitable for containing a fluid, in particular a lubricant, the central and peripheral test pieces extending at least in part in said cavity such that the contacts between the central test piece and the peripheral test pieces are immersed at least in part in the fluid.

7. A tribometer according to claim 1, wherein it comprises a circuit configured to establish circulation of a fluid in the cavity.

8. A tribometer according to claim 5, wherein it comprises a load-application device configured to apply a force on at least one of the support parts, and in particular on all three of them.

9. A tribometer according to claim 1, wherein the load-sharing device comprises two guide pulleys for guiding the belt, each being disposed between two drive pulleys.

10. A tribometer according to claim 1, wherein the load-sharing device comprises two load pulleys having the two ends of the belt secured respectively thereto.

11. A tribometer according to claim 10, wherein at least one of the load pulleys is driven in rotation by a strip secured at one end to said load pulley and at its other end to a moving carriage.

12. A tribometer according to claim 11, wherein the load-sharing device comprises a first membrane configured to drive displacement of the moving carriage.

13. A tribometer according to claim 12, wherein it comprises a pressure-regulator system configured to control the pressure of the first membrane.

14. A tribometer according to claim 2, wherein all three of the peripheral pieces present a shape selected in such a manner as to enable contact with the central test piece to be linear.

15. A tribometer according to claim 2, wherein said linear contact is a straight line segment.

16. A tribometer according to claim 13, wherein the system comprises a spring having a first end suitable for being moved by a motor and a second end secured to an arm configured to act on a second flexible membrane in communication with the first.

* * * * *